United States Patent [19]

Kobayashi

[11] Patent Number: 4,849,137

[45] Date of Patent: Jul. 18, 1989

[54] PROCESS FOR PRODUCING LYSOPHOSPHOLIPIDS CONTAINING SUBSTANTIALLY NO LYSOPHOSPHOLIPIDS EXCEPT LPC

[75] Inventor: Hideaki Kobayashi, Fuchu, Japan

[73] Assignee: Kewpie Kabushiki Kaisha, Tokyo, Japan

[21] Appl. No.: 82,333

[22] Filed: Aug. 6, 1987

[30] Foreign Application Priority Data

Apr. 9, 1987 [JP] Japan .................... 62-87347

[51] Int. Cl.$^4$ ............ C07F 9/02; C07F 9/10; A23J 7/00
[52] U.S. Cl. .................. 260/403; 260/412.4; 260/427; 260/428; 260/428.5
[58] Field of Search ............ 260/403, 412.4, 427, 260/428, 428.5

[56] References Cited

U.S. PATENT DOCUMENTS 2,864,848 12/1958 McArthur ............... 260/403
4,629,588 12/1986 Welsh et al. ............ 260/428

FOREIGN PATENT DOCUMENTS 0043018 1/1982 European Pat. Off. ........... 260/403
0054770 6/1982 European Pat. Off. ........... 260/403
0115981 8/1984 European Pat. Off. ........... 260/403
0217765 4/1987 European Pat. Off. ........... 260/403
1588863 4/1970 France ............................. 260/403
1191689 8/1986 Japan .............................. 260/403

Primary Examiner—Patrick P. Garvin
Assistant Examiner—E. D. Irzinski
Attorney, Agent, or Firm—Oblon, Spivak, McClelland, Maier & Neustadt

[57] ABSTRACT

Lysophospholipids containing substantially no lysophospholipids except LPC can be obtained by dissolving lysophospholipids in a polar solvent or a mixture of a polar solvent and a non-polar solvent, contacting the resulting solution with an ion exchanger, and then distilling off the solvent or the solvent mixture from the solution. The lysophospholipids thus obtained entail substantially no deterioration such as browning or emission of an unpleasant odor even after a long period of storage and therefore can be expected to have a wider application in numerous fields, especially in the fields of food, cosmetics and drugs.

6 Claims, No Drawings

PROCESS FOR PRODUCING LYSOPHOSPHOLIPIDS CONTAINING SUBSTANTIALLY NO LYSOPHOSPHOLIPIDS EXCEPT LPC

BACKGROUND OF THE INVENTION

The present invention relates to a novel process for producing lysophospholipids containing substantially no lysophospholipids except lysophosphatidylcholine (LPC).

The lysophospholipid is obtained by the removal of one fatty acid unit per molecule from a phospholipid and the introduction of a hydroxyl group in place thereof. The lysophospholipid, being more highly hydrophilic than the phospholipid, not only has good emulsifying capability inherent in the phospholipid but is said to be capable of forming spherical micelles to solubilize water-insoluble substances in transparent state, and is therefore expected to be applicable as a solubilizer in the fields of food, cosmetics and drugs.

Heretofore, the lysophospholipids have been produced generally by causing an enzyme to act on natural phospholipids or phospholipid-containing substances derived from organisms or by subjecting these to alkali hydrolysis. The lysophospholipid thus obtained is ordinarily in the form of a mixture containing lysophospholipids such as lysophosphatidylethanolamine (LPE), lysophosphatidylinositol (LPI) and lysophosphatidylserine (LPS) in addition to LPC.

Such a lysophospholipid mixture can per se be used as a natural surfactant or solubilizer but, when stored over a long period of time, turns gradually from ordinary pale yellow or white to brown and even gives out an unpleasant odor. Such a deterioration phenomenon has been found to become more notable as the content of lysophospholipids except LPC increases. Moreover, the higher the LPC content in the lysophospholipid, the more stable have emulsified or solubilized products obtained by using the lysophospholipid been found to be.

In view of the above, if lysophospholipids containing substantially no lysophospholipids except LPC could be produced, such products would be highly beneficial and valuable from a commercial point of view.

Since LPC is analogous to lysophospholipids except LPC in molecular structure and both of these lysophospholipids are surface active substances, the lysophospholipids except LPC cannot easily be removed from a lysophospholipid mixture by an ordinary simple substance separation method such as the solvent extraction method. Further, the removal from such a mixture is still more difficult because in respect of constituent fatty acids neither LPC nor the lysophospholipids except LPC comprise a single constituent fatty acid, but they have respectively specific compositions which are due to the starting materials.

While the removal of the target lysophospholipids is accompanied by the above described difficulties, the lysophospholipids except LPC can be removed with considerable accuracy, for example, by column chromatography with the use of silica gel or alumina at a laboratory level. It would be disadvantageous, however, to raise this level up to a commercial scale from the economic point of view including costs. Under such circumstances, an object of the present invention is to provide a process whereby lysophospholipids containing substantially no lysophospholipids except LPC can be produced on a commercial scale at low cost and yet by a simple procedure.

SUMMARY OF THE INVENTION

As a result of extensive research effort expended toward attaining the above object, I have found that, if lysophospholipids are dissolved in a polar solvent or a mixture of a polar solvent and a non-polar solvent and thereafter brought into contact with an ion exchanger, the ion exchanger will adsorb and remove lysophospholipids except LPC selectively and efficiently, and thus I have arrived at the present invention on the basis of this finding.

More specifically, the present invention provides a process for producing lysophospholipids containing substantially no lysophospholipids except LPC which comprises dissolving lysophospholipids in a polar solvent or a mixture of a polar solvent and a non-polar solvent, contacting the solution obtained with an ion exchanger, and then distilling off the solvent from the solution.

DETAILED DESCRIPTION OF THE INVENTION

The starting lysophospholipids to which the process of this invention is applied are lipid fractions containing lysophospholipids such as LPE, LPI and LPS in addition to LPC.

Specific examples of such lysophospholipids are (a) those obtained by causing an enzyme such as lipase (EC3, 1, 1, 3), phospholipase $A_1$ (EC3, 1, 1, 32) or phospholipase $A_2$ (EC3, 1, 1, 4) to act on natural phospholipids or phospholipid-containing substances derived from organisms, such as animal or plant tissue or microorganism cells containing a large quantity of phospholipids (e.g., egg yolk, bovine brain, porcine brain, soybean, rapeseed, Chlorella cells, and mould cells (including Cunninqhamella microorganism cells)), crude phospholipid extracts obtained from these animal or plant tissue or microorganism cells (e.g., commercially available soybean phospholipid and commercially available egg yolk phospholipid), and purified phospholipids thereof, or by subjecting these phospholipids or phospholipid-containing substances to alkali hydrolysis, both the enzymatic action and the alkali hydrolysis being intended for conversion of the phospholipids into lysophospholipids; or (b) those with specific fatty acid units obtained by the semisynthesis method which is a combination of the enzymatic treatment or alkali hydrolysis and chemical synthesis, for example, by subjecting purified egg yolk lecithin (containing about 80% of PC and about 18% of PE) to alkali hydrolysis for deacylation, re-esterifying the thus deacylated egg yolk lecithin with a specific fatty acid, and then treating the resultant egg yolk lecithin with phospholipase $A_2$ to obtain the desired lysophospholipid (containing about 80% of LPC and about 18% of LPE).

The solvent for the starting lysophospholipids used in the process of the present invention is a polar solvent, such as methanol, ethanol, propanol, acetone or water, or a mixture thereof with a non-polar solvent, such as n-pentane, n-hexane, n-heptane, chloroform, dichloromethane, ether, or benzene. A non-polar solvent alone cannot readily dissolve lysophospholipids and therefore effective removal of lysophospholipids except LPC cannot be expected. While the blending rate between the polar solvent and the non-polar solvent in the solvent mixture is not particularly limited, it is preferable that the rate of the polar solvent be higher for the above reason. For example, the rate of the non-polar solvent in the mixture may advantageously be 20% (v/v) or less.

The concentration of the lysophospholipids in the solvent, i.e., the concentration of the lysophospholipids in the solution obtained, is preferably about 1 to 10% (w/v). A concentration below 1% is not economical because the quantity of the solvent required is too great, but, if the concentration exceeds 10%, the lysophospholipids will become difficult to dissolve.

The ion exchanger used herein is not particularly limited as long as it is a solid capable of causing ion exchange in the above stated solvent. Examples of the ion exchangers are ion-exchange resins, ion-exchange gels, or structures comprising inorganic substrates such as silica gel and alumina and ion-exchange groups (electrically charged groups) covalently bonded onto the surfaces thereof. A variety of commercially available strongly or weakly acidic cationic exchangers or strongly or weakly basic anionic exchangers are suitably employed in the present invention.

Specific examples of such cationic exchangers are Amberlite IR-120B and IRC-50 (supplied by Rohm & Haas Co.); DuoLite C-20 and C-433 (supplied by Diamond Shamrock Corp.); Dowex HCR-S and CCR-2 (supplied by Dow Chemical Co.); and DIAION SK-1B and WK-10 (supplied by Mitsubishi Kasei K.K., Japan), while specific examples of such anionic exchangers are Amberlite IRA-400 and IRA-93; DuoLite A-101D and A-368; Dowex 11 and MWA-1; and DIAION SA-10A and WA-30. These ion exchangers may be used singly or may also be used either in the form of a mixture of two or more members irrespective of the species in any ratio or sequentially. For example, a mixture of one acidic ion exchanger and one basic ion exchanger in a ratio of 3:1 to 1:3 (w/w) may advantageously be used, and such a mode of practice is preferred. Advantageously, the acidic ion exchanger is prepared in H form while the basic ion exchanger is prepared in OH form in practical use in order to improve adsorption efficiency.

The quantity of the ion exchanger used can vary depending upon the quantity of the lysophospholipids except LPC contained in the starting lysophospholipids or the particular type of the ion exchanger selected. In general, however, the ion exchanger may advantageously be used ordinarily in a quantity at least threefold (v/w) that of the lysophospholipids except LPC contained in the starting lysophospholipids since the ion exchanger in less than threefold quantities is insufficient to afford the effect of removing the lysophospholipids except LPC. Preferably, the quantity of the ion exchanger is suitably selected in the range of from 5- to 40-fold (v/w) the quantity of the lysophospholipids except LPC in the starting material. Within this range, it is possible to reduce the quantity of the lysophospholipids except LPC to substantially trace amounts on a commercial scale. Thus, the use of the ion exchanger in excess is not even economical but rather tends to lower the yield of the desired end product.

The lysophospholipid solution may be brought into contact with the ion exchanger by passing the solution through a column packed with a predetermined quantity of the ion exchanger by a conventional method or by suspending a predetermined quantity of the ion exchanger in the solution with stirring. This contact is advantageously carried out at a temperature lower than the boiling point of the solvent from the point of view of the prevention of the evaporation of the solvent.

In accordance with the process of the present invention, the ion exchanger is caused to selectively adsorb the lysophospholipids except LPC by the above described contact, and the solvent used is then distilled off, for example, under reduced pressure, from the solution subsequently to the selective adsorption in the case of the solution which has been passed through the column, or after the ion exchanger is removed, for example, by filtration in the case of the solution which has been contacted with the ion exchanger by stirring.

According to the process of the present invention as is set forth hereinabove, the lysophospholipids except LPC in the starting lysophospholipids can be reduced very effectively and hence lysophospholipids containing substantially no such lysophospholipids can be produced. In addition, as will be apparent from the results of the experimental examples which will be described later, the content of the lysophospholipids except LPC in the starting lysophospholipids can be reduced to substantially trace amounts on a commercial scale with the use of the ion exchanger in a quantity about 5-fold (v/w) the lysophospholipid content except LPC. That is, only an extremely small quantity of resin is required and yet the overall operating procedures are remarkably simple. Accordingly, the present invention provides a process whereby lysophospholipids containing substantially no lysophospholipids except LPC, i.e., entailing no deterioration due to storage such as browning or emission of an unpleasant odor, can be produced on a commercial scale at low cost and yet by a simple procedure. Needless to say, the process of the present invention, if repeatedly practiced, can be carried out more suitably for the desired purpose.

Although this invention is not intended to be bound to any theory, the lysophospholipids except LPC can be effectively removed presumably because LPE, LPI, LPS and like lysophospholipids, due to the active group thereof, are more selectively adsorbed by the ion exchanger than LPC.

The lysophospholipids obtained by the process of the present invention, entailing substantially no deterioration such as browning or emission of an unpleasant odor even after a long period of storage, can be expected to have a wider application in numerous fields including, inter alia, the fields of food, cosmetics and drugs, for example, in solubilizing oil-soluble vitamins or flavors in various beverages, solubilizing perfumes in lotions or solubilizing various drugs in carriers.

In the case where purified lysophospholipids, for example, the purified lysophospholipids substantially free from neutral lipids obtained by the process of my co-pending Japanese Patent Appln. No. 177142/1986 (as will be illustrated hereinlater in the experimental examples), are used as the starting lysophospholipids in the process of the present invention, lysophospholipids having an LPC content of at least about 95% or consisting essentially of LPC can be obtained as the end products. These LPC products have the advantage of increasing the stability of emulsified or solubilized products obtained by using such LPC products and further can be expected to be applicable as starting materials for physiologically active lysophospholipids, for example, for carcinostatic agents.

Even in the case where crude lysophospholipids, for example, crude lysophospholipids containing neutral lipids, are used as the starting lysophospholipids in the process of the present invention, lysophospholipids having an LPC content of at least about 95% or consisting essentially of LPC can be finally obtained if the neutral lipids are removed by the process of the above mentioned Japanese Patent Appln. No. 177142/1986 after the process of this invention has been carried out.

When lysophospholipids obtained by causing an enzyme to act on natural phospholipids or phospholipid-containing substances derived from organisms are intended for use as the starting lysophospholipids in the process of the present invention, as long as lysophospholipids with substantially no residual enzyme activity obtained by the process of my another co-pending Japanese Patent Appln. No. 106329/1986 (as will be illustrated hereinlater in the experimental examples) are used as the starting lysophospholipids, the end products obtained will entail substantially no deterioration of quality due to residual enzyme activity.

Thus, the process of the present invention, if carried out in combination with the processes of my co-pending Japanese Patent Appln. Nos. 177142/1986 and 106329/1986 mentioned above, will afford products consisting essentially of LPC and having notably high storage stability, and such products can therefore have a much wider application in various fields.

Hereinafter, the present invention will now be described in more detail with reference to specific examples of practice. All percentages set forth herein are % by weight unless otherwise indicated.

EXAMPLE 1

(a) Preparation of crude lysophospholipids:

To 100 kg of egg yolk was added a solution of 5 kg of pancreatin (having phospholipase $A_2$ activity, supplied by Wako Junyaku K.K., Japan) dissolved in 10 kg of pure water, and the mixture was subjected to an enzyme reaction at 35 to 45° C. for 6 hours with stirring while the pH thereof was maintained at 7.0 to 8.0 with a 1 N aqueous solution of sodium hydroxide. The enzyme reaction product obtained was freeze-dried as it was in accordance with the process of Japanese Patent Appln. No. 106329/1986 to obtain 47.2 kg of dried egg yolk having a water content of 1.6%.

To this dried egg yolk was added 400 liters of methanol, and extraction was carried out at 30 to 40° C. for 30 minutes with stirring, followed by filtration. The extract thus obtained was concentrated under vacuum to obtain 21.8 kg of a yellow paste-like substance with substantially no residual enzyme activity.

The lipid composition of this substance (crude lysophospholipids) was then analysed by means of IATROSCAN TH-10 (TLC/FID) (supplied by Yatron K.K., Japan) under the following measurement conditions, whereupon this substance was found to comprise 74.1% of neutral lipids and 25.9% of phospholipids (19.2% of LPC, 4.8% of LPE and 1.9% of other phospholipids).

Measurement Conditions
Rod: Chromarod S-II (Silica gel)
Developing Solvent: Chloroform:Methanol:Water 80:35:3 (v/v/v)
Developing Distance: 10 cm
Measurement 500 mg of each test sample was dissolved in 10 ml of a 2:1(v/v) chloroform-methanol solution mixture, and 1 μl of the resulting solution was spotted on a rod. The sample solution was developed, air-dried and thereafter analysed by means of IATROSCAN. The lipid composition was determined on the basis of the area ratio of the respective peaks.

(b) Preparation of purified lysophospholipids:

In accordance with the process of Japanese Patent Appln. No. 177142/1986, the following purification procedure was carried out.

5 kg of the crude lysophospholipids obtained above were taken out, and 50 liters of acetone was added thereto. The mixture was gently stirred, and 25 ml of conc. hydrochloric acid was added thereto. The resulting mixture was vigorously stirred at 10° C. for 30 minutes, and the precipitate formed was filtered to obtain acetone insolubles. To these insolubles was added 50 liters of acetone, and the mixture was again stirred under the same conditions and subjected to filtration to obtain acetone insolubles. This procedure was repeated once more, and the solvent was removed under vacuum from the acetone insolubles obtained to yield 1.10 kg of a white powder.

The lipid composition of this powder was determined by means of IATROSCAN TH-10 in accordance with the above measurement method (the lipid composition being analysed by the above method in all the examples of the present invention), whereupon the white powder was found to comprise 1.5% of neutral lipids and 98.5% of phospholipids (82.1% LPC, 15.2% of LPE and 1.2% of other phospholipids).

(c) Practice of the process of the present invention:

600 g of this white powder was taken out and dissolved in 12 liters of methanol. To the resulting solution were added 600 ml each of ion exchange resins, Amberlite IR-120B (H type) and Amberlite IRA-400 (OH type), and the mixture was gently stirred at 20° to 40° C. for one hour and then filtered to remove the ion exchange resins. Subsequently, the solvent used was distilled off under reduced pressure to obtain 426 g of the end product white powder.

This product was found, upon analysis of the lipid composition thereof, to comprise 2.3% of neutral lipids, 97.7% of LPC and trace amounts of LPE. Accordingly, this product can be said to be lysophospholipids consisting essentially of LPC, i.e., an LPC product of high purity.

EXAMPLE 2

400 g of the white powder obtained in the preceding Example 1, (b) was taken out and dissolved in 12.5 liters of a 90:10 (v/v) ethanol-chloroform mixture. To the resulting solution were added ion exchange resins: 400 ml of DuoLite C-20 (H type) and 600 ml of DuoLite A-101D (OH type). The mixture was gentle stirred at 20° to 40° C. for one hour and then filtered to remove the ion exchange resins. Thereafter, the solvent used was distilled off under reduced pressure to obtain 272 g of a white powder product (LPC product).

This product was found, upon analysis of the lipid composition thereof, to comprise 2.8% of neutral lipids, 97.2% of LPC and trace amounts of LPE.

EXAMPLE 3

(a) Preparation of crude lysophospholipids:

To 60 kg of a commercially available soybean phospholipid product (38% neutral lipids and 62% phospholipids) was added a solution of 100 g of a phospholipase $A_2$ preparation dissolved in 3 liters of pure water, and the mixture was subjected to an enzyme reaction at 55° C. for 48 hours with stirring while the pH thereof was maintained at 8.0 to 8.5 with a 1 N aqueous solution of calcium hydroxide. The enzyme reaction product obtained was subjected to the Folch extraction method (Yasuhiko Fujino, "Seibutsu-kagaku Jikken-ho 9, Shishitsu Bunseki-ho Nyumon (the Elementary Lipid Analysis: Biochemical Experimental Method 9)", Gakkai Shuppan Center (1978), p. 42) to obtain 56.0 kg of crude lysophospholipids.

The crude lysophospholipids thus obtained were found, upon analysis of the lipid composition thereof, to comprise 39.0% of neutral lipids and 61.0% of phospholipids (LPC +LPE +LPI +LPS totalling 58.5%).

(b) Preparation of purified lysophospholipids:

The following purification procedure was again carried out in accordance with the process of Japanese Patent Appln. No. 177142/1986.

To 56.0 kg of the crude lysophospholipids thus obtained was then added 500 liters of acetone, and the mixture was gently stirred. To the resulting solution was added 600 ml of glacial acetic acid, and the mixture was vigorously stirred at 10° C. for 30 minutes. The precipitate formed was filtered to obtain acetone insolubles. To these insolubles was added 500 liters of acetone, and the mixture was again stirred under the same conditions and subjected to filtration to obtain acetone insolubles. This procedure was repeated once more, and the solvent was removed under vacuum from the thus obtained acetone insolubles to obtain 24.0 kg of a pale yellow powder.

This product was found, upon analysis of the lipid composition thereof, to comprise 1.5% of neutral lipids, 26.8% of LPC and 71.7% of other lysophospholipids (e.g., LPE, LPI and LPS).

(c) Practice of the process of the present invention:

24.0 kg of this pale yellow powder was dissolved in 980 liters of a 95:5 (v/v) ethanol-water mixture with stirring (insolubles which correspond to approximately 30% of the lysophospholipids except LPC being removed by filtration). To the resulting solution were added ion exchange resins: 30 liters of Amberlite IR-120B (H type) and 45 liters of Amberlite IRA-400 (OH type), and the mixture was gently stirred at 20° to 40° C. for one hour and then filtered to remove the ion exchange resins. The solvent used was thereafter substantially distilled off under reduced pressure. To the substance obtained was added 80 liters of acetone, and the mixture was vigorously stirred at 10° to 30° C. for one hour. The precipitate formed was filtered to obtain acetone insolubles. The solvent was removed under vacuum from the thus obtained acetone insolubles to obtain 5.1 kg of a white powder.

This product was found, upon analysis of the lipid composition thereof, to comprise 1.7% of neutral lipids, 94.5% of LPC and 3.8% of other lysophospholipids.

EXAMPLE 4

(a) Preparation of crude lysophospholipids:

To 50 kg of egg yolk was added a solution of 2.5 kg of pancreatin (having phospholipase $A_2$ activity, supplied by Wako Junyaku K.K., Japan) dissolved in 5 kg of pure water, and the mixture was subjected to an enzyme reaction at 35° to 45° C. for 6 hours with stirring while the pH thereof was maintained at 7.0 to 8.0 with a 1 N aqueous solution of sodium hydroxide. The enzyme reaction product obtained was freeze-dried as it was in accordance with the process of Japanese Patent Appln. No. 106329/1986 to obtain 23.0 kg of dried egg yolk having a water content of 2.1%.

To this dried egg yolk was added 200 liters of methanol, and extraction was carried out at 30° to 40° C. for 30 minutes with stirring followed by filtration. The extract thus obtained was concentrated under vacuum to obtain 10.3 kg of a yellow paste-like substance with substantially no residual enzyme activity.

This substance (crude lysophospholipids) was found, upon analysis of the lipid composition thereof, to comprise 71.8% of neutral lipids and 28.2% of phospholipids (21.0% of LPC, 5.1% of LPE and 2.1% of other phospholipids).

(b) Practice of the process of the present invention:

10.2 kg of the crude lysophospholipids were dissolved in 50 liters of methanol, and to the resulting solution were added 5.5 liters each of ion exchange resins Amberlite IR-120B (H type) and Amberlite IRA-400 (OH type). The mixture was gently stirred at 20° to 40° C. for one hour and then filtered to remove the ion exchange resins. The solvent used was thereafter substantially distilled off under reduced pressure.

The substance thus obtained was found, upon analysis of the lipid composition thereof, to comprise 70.5% of neutral lipids and 29.5% of phospholipids (29.2% of LPC, trace amounts of LPE and 0.3% of other phospholipids).

(c) Purification (Removal of neutral lipids):

To the substance obtained in the manner described above was then added 20 liters of acetone, and the mixture was vigorously stirred at 20° C. for 30 minutes. The precipitate formed was filtered to obtain acetone insolubles. This procedure was repeated twice, and the solvent was removed under vacuum from the thus obtained acetone insolubles to obtain 1.96 kg of a white powder product (LPC product).

This product was found, upon analysis of the lipid composition thereof, to comprise 3.4% of neutral lipids, 96.6% of LPC and trace amounts of LPE.

EXAMPLE 5

(a) Preparation of crude lysophospholipids:

The procedure of Example 1 was followed.

(b) Preparation of purified lysophospholipids:

The procedure of Example 1 was followed.

(c) Practice of the process of the present invention:

100 g of the white powder (comprising 1.2% of neutral lipids and 93.8% of phospholipids (81.9% of LPC, 16.0% LPE and 2.1% of other phospholipids)) obtained in the procedure (b) was dissolved in 5 liters of a 95:5 (v/v) ethanol-water mixture.

Separately, 300 ml each of ion exchange resins Amberlite IR-120B (H type) and Amberlite IRA-400 (OH type) were mixed homogeneously and charged into a glass column (5 cm dia.×40 cm ht.) which was then washed with 1 liter of a 95:5 (v/v) ethanol-water mixture passed from the top thereof, whereupon the column was ready for use.

The solution prepared by the above procedure was passed through the column from the top thereof at room temperature at a flow rate of from 10 to 20 ml/min. The eluates obtained were collected, and the solvent was distilled off under reduced pressure to obtain 74.2 g of a white powder as the end product.

This product was found, upon analysis of the lipid composition thereof, to comprise 1.9% of neutral lipids, 98.1% of LPC and trace amounts of LPE.

All of the end products obtained in Examples 1 through 5 did not turn brown or give out an unpleasant odor even after storage over a period as long as one year at room temperature.

The following Test Examples are incorporated herein to show that, in the process of the present invention, the quantity of the ion exchange resins used may be suitably determined according to the content of the lysophospholipids except LPC in the starting material irrespective of whether a purified product containing substantially no neutral lipids is used as starting lysophospholipids (Test Example 1) or a crude product containing neutral lipids is used as such (Test Example 2).

TEST EXAMPLE 1

100 g of the white powder (comprising 1.5% of neutral lipids, 82.1% of LPC, 15.2% of LPE and 1.2% of other phospholipids) obtained in Example 1, (b) was dissolved in 2.5 liters of methanol, and the resulting solution was divided into aliquots each of 0.5 liter. To the five aliquots thus obtained was apportioned an equivalent mixture of ion exchange resins Amberlite IR-120B (H type) and Amberlite IRA-400 (OH type) in 3-fold, 5-fold, 25-fold, 40-fold and 50-fold (v/w) quantities for the total content of the lysophospholipids except LPC in the white powder, and all of the aliquots were gently stirred at 30° C. for one hour and then filtered to remove the ion exchange resins.

A very small portion of each of the five samples thus obtained was subjected to analysis of the lipid composition thereof while the remaining substantial portion of each of the respective samples was subjected to solvent removal under reduced pressure to determine the yield of the white powder obtained. The lipid compositions were analyzed under the conditions in Example 1 set forth hereinbefore except that the solutions after removal of the resins were used as samples without further treatment.

The results obtained were as shown in Table 1 below.

TABLE 1

| Measurement item | | White powder (Control) (%) | Quantity of ion exchange resin mixture added | | | | |
|---|---|---|---|---|---|---|---|
| | | | 3-Fold (9.8 ml) (%) | 5-Fold (16.4 ml) (%) | 25-Fold (82.0 ml) (%) | 40-Fold (131.2 ml) (%) | 50-Fold (164.0 ml) (%) |
| Lysophospholipid composition | LPC | 82.1 | 94.2 | 97.6 | 98.6 | 97.9 | 98.2 |
| | LPE | 15.2 | 4.2 | 1.0 | trace | trace | trace |
| | Others | 1.2 | 1.0 | 0.5 | 0.3 | 0.4 | 0.2 |
| Yield | | (100) | 79.1 | 73.0 | 72.0 | 70.6 | 61.9 |

TEST EXAMPLE 2

100 g of the yellow paste-like substance obtained in Example 4, (a) (comprising 71.8% of neutral lipids, 21.0% of LPC, 5.1% of LPE and 2.1% of other phospholipids) was dissolved in 2.5 liters of methanol, and the resulting solution was divided into aliquots each of 0.5 liter. To the five aliquots thus obtained was apportioned an equivalent mixture of ion exchange resins Amberlite IR-120B (H type) and Amberlite IRA-400 (OH type) in 3-fold, 5-fold, 25-fold, 40-fold and 50-fold (v/w) quantities for the total content of the lysophospholipids except LPC in the yellow paste-like substance, and all of the aliquots were gently stirred at 30° C. for one hour and then filtered to remove the ion exchange resins.

A very small portion of each of the five samples thus obtained was subjected to the analysis of the lipid composition thereof without further treatment as in Test Example 1 set forth above, while the remaining substantial portion of each sample was subjected to solvent removal under reduced pressure to determine the yield of the pale yellow paste-like substance obtained.

Presented in Table 2 are the results obtained.

The samples treated with 25-fold and 40-fold quantities of ion exchange resin mixtures were further treated with acetone (stirred vigorously in 200 ml of acetone at 20° C. for 30 minutes and then filtered to obtain acetone insolubles), and the solvent was removed under vacuum, whereby white powder products (LPC products) containing substantially no neutral lipids (1.0% or less) were obtained. The lipid compositions were 0.7% of neutral lipids, 99.3% of LPC and trace amounts of LPE for the former while 0.9% of neutral lipids, 99.1% of LPC and trace amounts of LPE for the latter.

TABLE 2

| Measurement item | | Yellow paste-like substance (Control) (%) | Ion exchange resin mixture | | | | |
|---|---|---|---|---|---|---|---|
| | | | 3-Fold (4.3 ml) (%) | 5-Fold (7.2 ml) (%) | 25-Fold (36.0 ml) (%) | 40-Fold (57.6 ml) (%) | 50-Fold (72.0 ml) (%) |
| Neutral lipid | | 71.8 | 72.0 | 71.3 | 71.5 | 71.4 | 71.6 |
| Lysophospholipid composition | LPC | 21.0 | 22.4 | 26.7 | 28.2 | 28.2 | 28.1 |
| | LPE | 5.1 | 4.1 | 1.2 | trace | trace | trace |
| | Others | 2.1 | 1.5 | 0.8 | 0.3 | 0.4 | 0.3 |
| Yield | | (100) | 94.0 | 90.6 | 87.4 | 85.2 | 71.7 |

From the data obtained in Test Examples 1 and 2 described above, it is apparent that, in the process of the present invention, the quantity of the ion exchange resins used may be suitably determined according to the content of the lysophospholipids except LPC in the starting material irrespective of whether the starting lysophospholipids are crude products or purified products, 5- to 40-fold quantities (v/w) being especially effective for removal of lysophospholipids except LPC. It is to be understood, on the other hand, that the ion exchange resins in 40-fold quantity or more tend to reduce the yields of the desired end products although the removal effect increases.

I claim:

1. A process for producing lysophospholipids containing substantially no lysophospholipids except LPC (lysophosphatidylcholine) which comprises dissolving lysophospholipids in a polar solvent or a mixture of a polar solvent and a non-polar solvent, contacting the resulting solution with an ion exchanger selected from the group consisting of strongly acidic cationic, weakly acidic cationic, strongly basic anionic and weakly basic anionic exchangers, and then distilling off the solvent or the solvent mixture from the solution.

2. A process as claimed in claim 1, wherein the starting lysophospholipids are purified lysophospholipids containing substantially no neutral lipids.

3. A process as claimed in claim 1, wherein the starting lysophospholipids are crude lysophospholipids containing neutral lipids.

4. A process as claimed in claim 3, wherein the neutral lipids are removed after the solvent has been distilled off.

5. A process as claimed in claim 1, wherein the ion exchanger is used in a quantity at least threefold (v/w) the content of the lysophospholipids except LPC in the starting lysophospholipids.

6. A process as claimed in claim 5, wherein the ion exchanger is used in a quantity ranging from 5- to 40-fold (v/w) the content of the lysophospholipids except LPC in the starting lysophospholipids.

* * * * *